United States Patent [19]
Ogino

[11] Patent Number: 5,247,340
[45] Date of Patent: * Sep. 21, 1993

[54] FLOW IMAGING CYTOMETER

[75] Inventor: Shinichi Ogino, Hyogo, Japan

[73] Assignee: TOA Medical Electronics Co., Ltd., Japan

[*] Notice: The portion of the term of this patent subsequent to Oct. 27, 2009 has been disclaimed.

[21] Appl. No.: 755,303

[22] Filed: Sep. 5, 1991

[30] Foreign Application Priority Data

Feb. 27, 1991 [JP] Japan ................... 3-033189

[51] Int. Cl.⁵ ............... G01N 33/48; G01N 21/64; G06K 9/20
[52] U.S. Cl. .................... 356/73; 250/461.2; 356/23; 356/39; 356/417
[58] Field of Search .......... 356/23, 39, 72, 73, 356/318, 417; 250/461.2; 382/6

[56] References Cited

U.S. PATENT DOCUMENTS

| | | | |
|---|---|---|---|
| 3,826,364 | 7/1974 | Bonner et al. | 356/73 |
| 4,243,318 | 1/1981 | Stohr | 356/43 |
| 4,338,024 | 7/1982 | Bolz et al. | 356/23 |
| 4,573,796 | 3/1986 | Martin et al. | 356/39 |
| 4,643,566 | 2/1987 | Ohe et al. | 356/72 |
| 4,786,165 | 11/1988 | Yamamoto et al. | 356/23 |
| 4,887,721 | 12/1989 | Martin et al. | 209/579 |
| 5,053,626 | 10/1991 | Tillotson | 356/417 |
| 5,159,397 | 10/1992 | Kosaka et al. | 356/39 |
| 5,159,398 | 10/1992 | Maekawa et al. | 356/39 |

FOREIGN PATENT DOCUMENTS 467714 6/1974 Austria.
3705876 4/1988 Fed. Rep. of Germany.

OTHER PUBLICATIONS

Cytometry (The Journal of the Soc. for Analytical Cytology) 9 (1988) Nov., No. 6, New York N.Y., USA "Imaging System for Morphometric Assessment of Absorption or Fluorescence in Stained Cells", B. Jaggi et al., pp. 566-572.

Primary Examiner—Richard A. Rosenberger
Attorney, Agent, or Firm—Pearne, Gordon, McCoy & Granger

[57] ABSTRACT

A flow imaging cytometer has an image capturing area for capturing the white-light image of a cell, and an image capturing area for capturing a fluorescent image of the same cell. The two image capturing areas are positionally offset from each other so that both images can be obtained in an excellent state with little mutual influence from the two types of light. Based upon detection of a cell using light from a light source for monitoring cell flow-through, a light source for exciting fluorescence and a strobe light source for emitting the white light area actuated after respective prescribed time delays. To this end, the cytometer incorporates a delay-pulse generating circuit serving as control means.

6 Claims, 6 Drawing Sheets

FLOW IMAGING CYTOMETER

BACKGROUND OF THE INVENTION

1. Field of the Invention

This invention relates to an apparatus for forming a particle-containing specimen solution such as blood or urine into a flat sheathed flow, irradiating the flat flow of the specimen solution with pulsed light to obtain a still picture, and applying imaging processing to perform analysis such as classification and enumeration of the particle components contained in the specimen solution. More particularly, the invention relates to a flow imaging cytometer, which is a particle image analyzer, adapted so as to constantly monitor an image capturing area of the flat specimen flow, irradiate the particles with light when they reach the image capturing area, and acquire a fluorescent image and/or white-light image of the particle components in an efficient manner.

2. Description of the Prior Art

A technique known in the art is to subject particles such as stained cells to exciting light and perform analysis such as classification of the particles by detecting fluorescence emitted by the particles. Specific examples of apparatus which employ this technique are flow cytometers and microscopes.

A flow cytometer is capable of detecting the amount of fluorescence emitted by individual particles.

A detailed fluorescent image can be observed by using a microscope. In addition, an arrangement is available in which the fluorescent image obtained is subjected to image processing. Furthermore, the specification of Japanese Patent Application Laid-Open (KOKAI) No. 63-269875 discloses an image capturing apparatus whereby images can be acquired using three types of light, namely ultraviolet light, visible light and infrared light.

An apparatus for acquiring the images of particles flowing as a flat stream and analyzing the particles by image processing is disclosed in the specifications of Japanese Patent Application Laid-Open No. 57-500995 and U.S. Pat. No. 4,338,024.

Further, the present applicant has previously filed an application for an apparatus adapted so as to constantly monitor an image capturing area, detect particles in the flow when they arrive at this area, and acquire images of the particles in efficient fashion.

SUMMARY OF THE INVENTION

Though the conventional flow cytometer exhibits a high processing capability per unit time, the fluorescence from particles can be obtained only as a gross value, and it is not possible to acquire detailed information as to which portions of a particle are emitting fluorescence and the degree of this fluorescence. Though a large quantity of information can be obtained using a microscope, pretreatment is laborious and a high processing speed cannot be obtained.

Accordingly, an object of the present invention is to provide a flow imaging cytometer which overcomes these difficulties encountered in the prior art.

Another object of the present invention is to provide a flow imaging cytometer having a high analyzing capability and adapted to obtain, efficiently and at high speed, a large quantity of particle information which includes detailed information relating to individual particles.

According to the present invention, the foregoing objects are attained by providing a flow imaging cytometer comprising a flow cell formed to include a flat flow path for causing a specimen solution containing particle components to be sensed to flow as a flat stream, a first and third light source arranged on a first side of the flow cell for irradiating the specimen solution in the flow cell with pulsed light, first and third image capturing means arranged on a second side of the flow cell for capturing still pictures of the particle components in the specimen solution irradiated by the first and third light sources, respectively, a second light source arranged on the first side of the flow cell for irradiating the specimen solution in the flow cell with light constantly, second image capturing means arranged on the second side of the flow cell for capturing an image of the specimen solution irradiated by the second light source, processing means for executing prescribed analysis based upon image data from the image capturing means, and control means for detecting the particle components based upon the image data from the second image capturing means, and on the basis of such detection, for actuating the first and third light sources after respective prescribed time delays, wherein the first and third image capturing means each has a two-dimensional image capturing area on the flow of the specimen solution, the second image capturing means has a linear image capturing area on the flow of the specimen solution, the image capturing area of the second image capturing means is formed so as to cross the flow of the specimen solution within the image capturing areas of the first image capturing means, and the first light source is caused to perform irradiation within the image capturing area of the first image capturing means and outside the image capturing area of the third image capturing means.

In this arrangement, the flow-imaging cytometer is characterized in that the second light source can be one which emits infrared light.

In another aspect of the present invention, the foregoing objects are attained by providing a flow imaging cytometer comprising a flow cell formed to include a flat flow path for causing a specimen solution containing particle components to be sensed to flow as a flat stream, a first light source arranged on a first side of the flow cell for irradiating the specimen solution in the flow cell with light quantity of which is switched, first image capturing means arranged on a second side of the flow cell for capturing still pictures of particle components in the specimen solution irradiated with high-luminance pulsed light from the first light source, second image capturing means arranged on the second side of the flow cell for capturing images of particle components in the specimen solution irradiated continuously with low-luminance light from the first light source, a second light source arranged on the first side of the flow cell for irradiating the specimen solution in the flow cell with pulsed light, third image capturing means arranged on the second side of the flow cell for capturing still pictures of particle components in the specimen solution irradiated continuously with light from the second light source, processing means for executing prescribed analysis based upon image data from the capturing means, and control means for detecting the particle components based upon the image data from the second image capturing means, and on the basis of such detection, for switching over the luminance of the first light source and actuating the second light source after respective prescribed time delays, wherein the first image capturing means has a two-dimensional image capturing area on the flow of the specimen solution, the second image capturing means has a linear image capturing area on the flow of the specimen solution, the image capturing area of the second image capturing means is formed so as to cross the flow of the specimen solution within the image capturing areas of the first image capturing means, and the first light source is caused to perform irradiation within the image capturing area of the first image capturing means and outside the image capturing area of the third image capturing means.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

Preferred embodiments of the present invention will now be described in detail with reference to the accompanying drawings.

Figure 1:
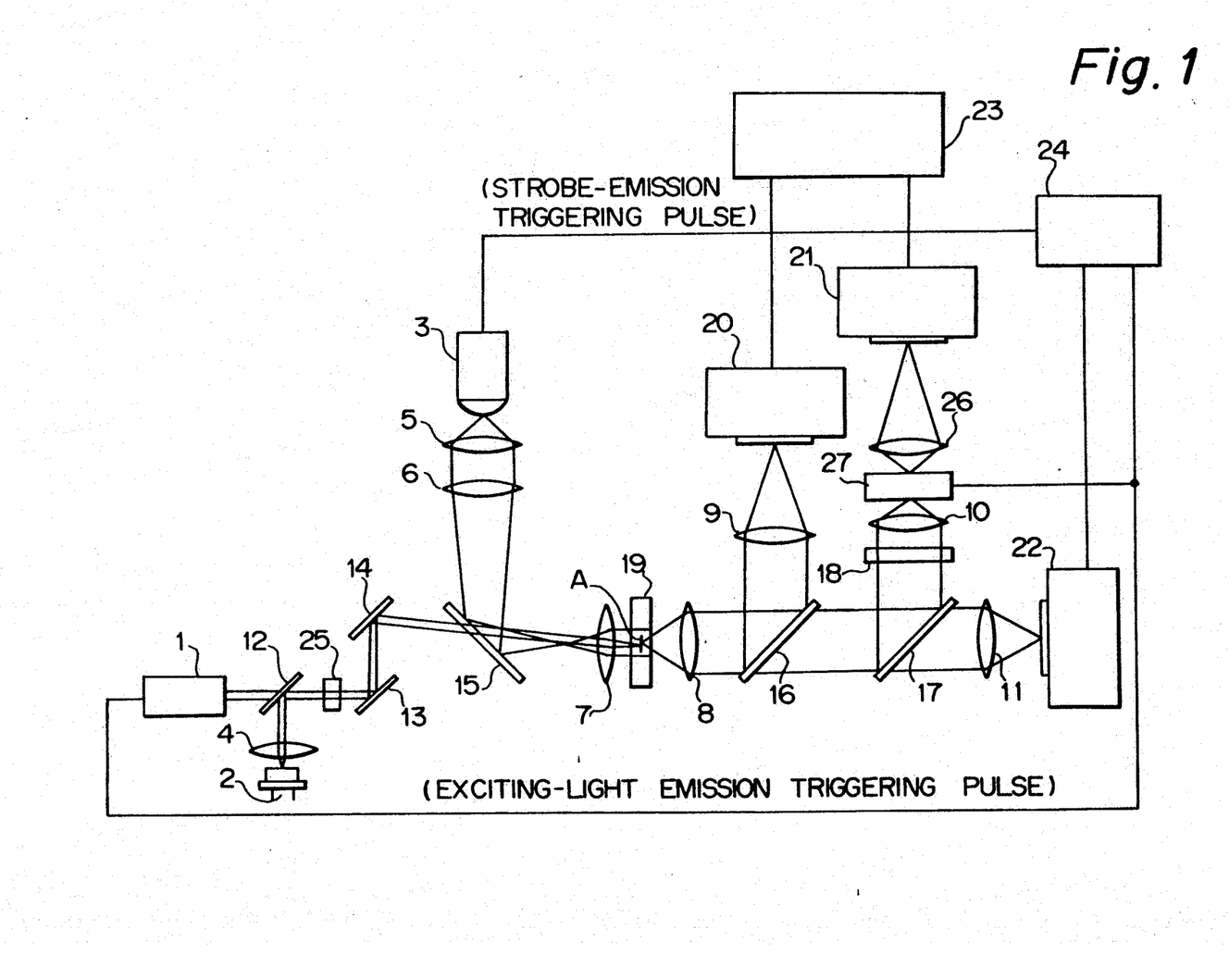
FIG. 1 is a block diagram illustrating the construction of a flow imaging cytometer according to an embodiment of the present invention.
Figure 2:
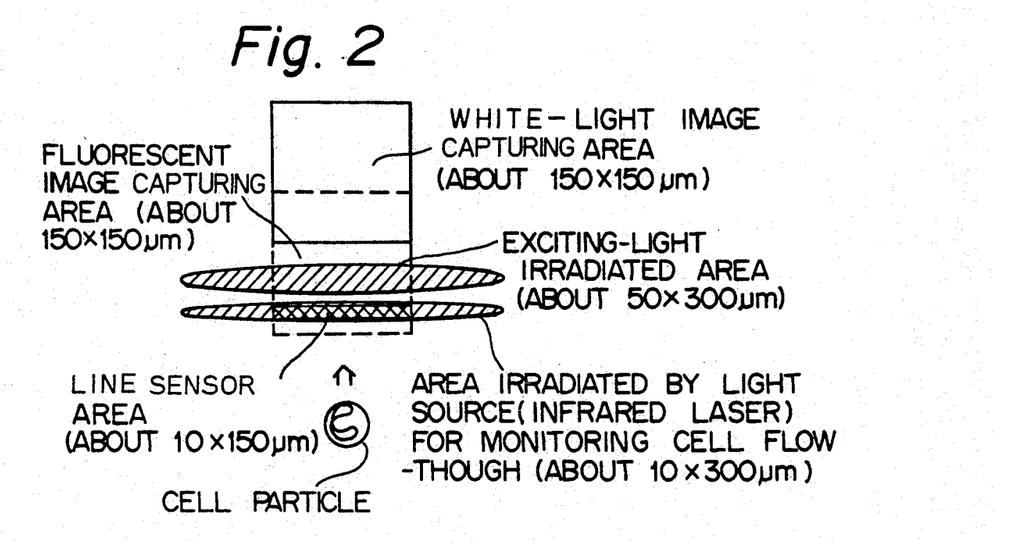
FIG. 2 is a explanatory view illustrating an example of light-irradiated areas and image capturing areas of the flow cell shown in FIG. 1.
Figure 3:
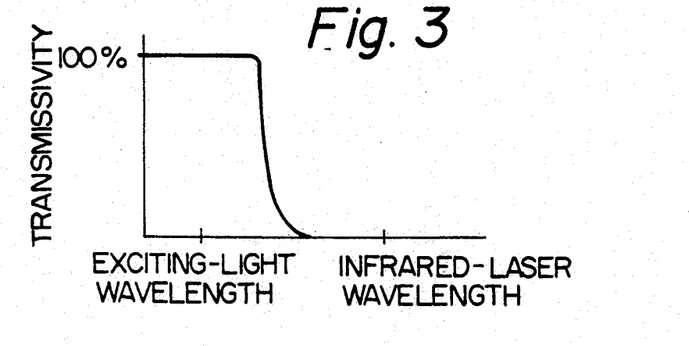
FIG. 3 is a diagram illustrating an example of the characteristic of a dichroic mirror.
Figure 4:
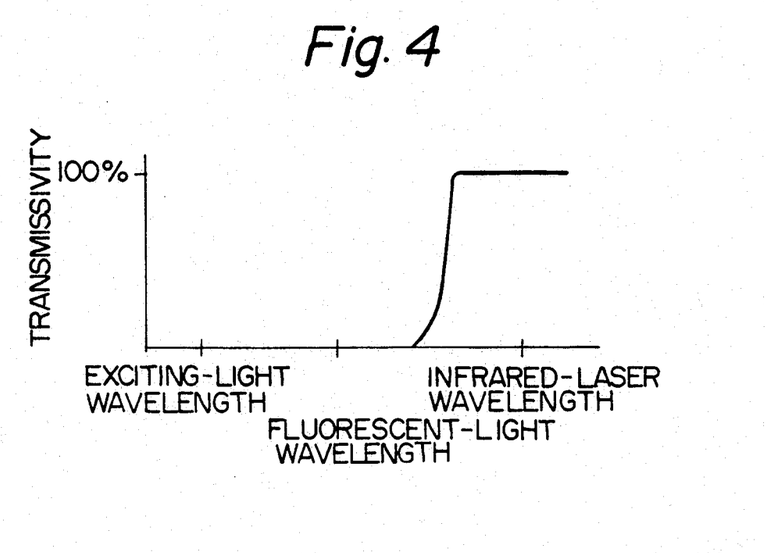
FIG. 4 is a diagram illustrating an example of the characteristic of another dichroic mirror.

A flow imaging cytometer according to a preferred embodiment of the present invention shown in FIG. 1 includes three light sources, namely an exciting light source 1 for exciting fluorescence, a light source 2 for monitoring passage of cells through the cytometer, and a strobe light source 3 for white-light photography. The light from the exciting light source 1 passes through a dichroic mirror 12 and enters to a light-shaper 25, where the light is acted upon by a cylindrical lens, a prism and other elements so as to be formed into an elongated elliptical shape perpendicular to the traveling direction of cell particle flowing through the cytometer. The resulting light then passes through mirror/prism units 13, 14 and enters to a condenser lens 7, which condenses the light at the position shown in FIG. 2 on a flat flow A of the specimen solution within a flow cell 19. The light from the cell flow-through monitoring light source 2 (which is an infrared semiconductor laser in this embodiment) collimated by a collimator lens 4 and then reflected by the dichroic mirror 12, after which the reflected light is formed into an elongated elliptical shape in the same manner as the light from light source 1. This light is then condensed at the position shown in FIG. 2 by the mirror/prism units 13, 14 and condenser lens 7. The light from the light source 3 (a strobe light in this embodiment) for white-light photography is collimated by a collimator lens 5 and condensed by a condenser lens 6, after which the condensed light is bent at an angle of 90° by a half-mirror 15 and collimated by a condenser lens 7, thereby uniformly illuminating the entirety of the white-light image capturing area (this is referred to generally as Köhler illumination).

The exciting light from the irradiation area of the light source 1 and the fluorescent light from a cell passes though an objective lens 8 and a half-mirror 16 to be bent at an angle of 90° by a dichroic mirror 17, after which only the fluorescent light is extracted by a filter 18 which filters out the exciting light. The extracted fluorescent light is acted upon by a projecting lens 10 to form an image on the photoelectric converting surface of an image intensifier 27. The image intensifier 27 is actuated in synchronization with an exciting-light trigger, thereby amplifying the intensity of the entrant light by a factor of $10^3$ to $10^6$ and forming an image on its fluorescent surface. This image is formed on an image sensor within a video camera 21 via a relay lens 26, whereby a fluorescent image is obtained.

Transmitted light from the white-light image capturing area passes though an objective lens 8 and is then bent at an angle of 90° by the half-mirror 16 to have its image formed on an image sensor within a video camera 20 by a projecting lens 9, whereby a white-light image is obtained. By setting the projecting lens 9 and the video camera 20 appropriately at this time, any influence upon the white-light image capturing area is eliminated in such a manner that the exciting-light irradiation area will not fall within the white-light image capturing area.

The transmitted light from the light source 3 passes through an objective lens 8, half-mirror 16 and dichroic mirror 17, after which it is formed on a CCD line sensor 22 by a projecting lens 11. A voltage conforming to the quantity of light accumulated is successively extracted from the CCD pixel by pixel. The scanning period of every line is several tens of microseconds. Therefore, by setting the amount of cell movement, namely the flow velocity of the sheathed flow, to a suitable value, the cells which pass through the monitoring area can be monitored without any cells being missed.

A suitable time after a cell is sensed by the line sensor 22, the light source 1 irradiates the cell, then the strobe light source 3 irradiates the cell following a further delay. As a result, both a fluorescent image and a white-light image can be obtained.

Figure 5:
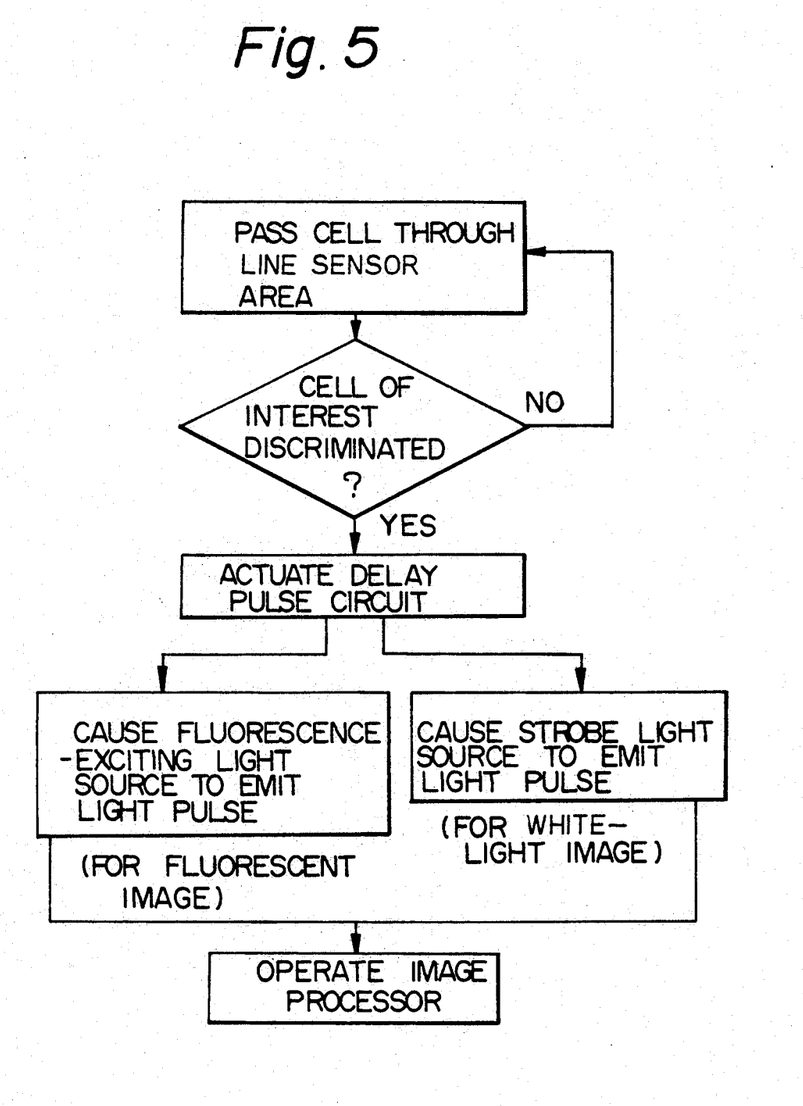
FIG. 5 is a measurement flowchart associated with the flow imaging cytometer of the present invention.

FIG. 5 is a flowchart illustrating measurement flow according to this embodiment.

Assume that the width of the image capturing area of the CCD line sensor in the direction of flow is 1 μm, the scanning period of the line sensor is 33 μsec, the flow velocity of the sheathed flow is 10 μm/33 μsec, and the size of a leukocyte is 15 μm. Under these conditions, one scan will always be made during transit of the leukocyte through the image capturing area of the line sensor. (It has been confirmed by calculation that the purpose can be attained if the flow velocity is less than 15 μm/33 μsec.) It is determined by such scanning whether the cell passing through the image capturing area is a cell of interest.

If the time from the start of scanning by the line sensor until discrimination of a cell is 100 μsec, then the cell will travel about 30 μm in this period of time. This means that the exciting-light irradiated area and the line sensor area should be set at positions more than 30 μm apart. If this distance is made 50 μm, the time required for a cell to travel 50 μm will be 165 μsec. The time (165 μsec) for transit from the line sensor area to the exciting-light irradiated area minus the aforementioned discrimination time of 100 μsec is 65 μsec. Accordingly, the light source 1 should be made to emit one light pulse 65 μsec after flow-through of a cell has been discriminated.

Further, assume that the distance between the exciting-light irradiated area and the white-light image capturing area is 50 μm. Since the time needed for a cell to travel this distance is 165 μsec, as set forth above, the light source 3 should be made to emit light 230 μsec after discrimination of cell flow-through. If it is desired that the cell image appear at the center of the white-light image capturing area, then the light source 3 should be made to emit light approximately 500 μsec after discrimination of cell flow-through.

The foregoing will make it possible to obtain both a white-light image and a fluorescent image of the same cell.

By analyzing both images using an image analyzer (image processor) 23, processing can be executed to present a three-dimensional display of fluorescent intensity distribution within a cell of a three-dimensional display of fluorescent intensity.

Figure 6:
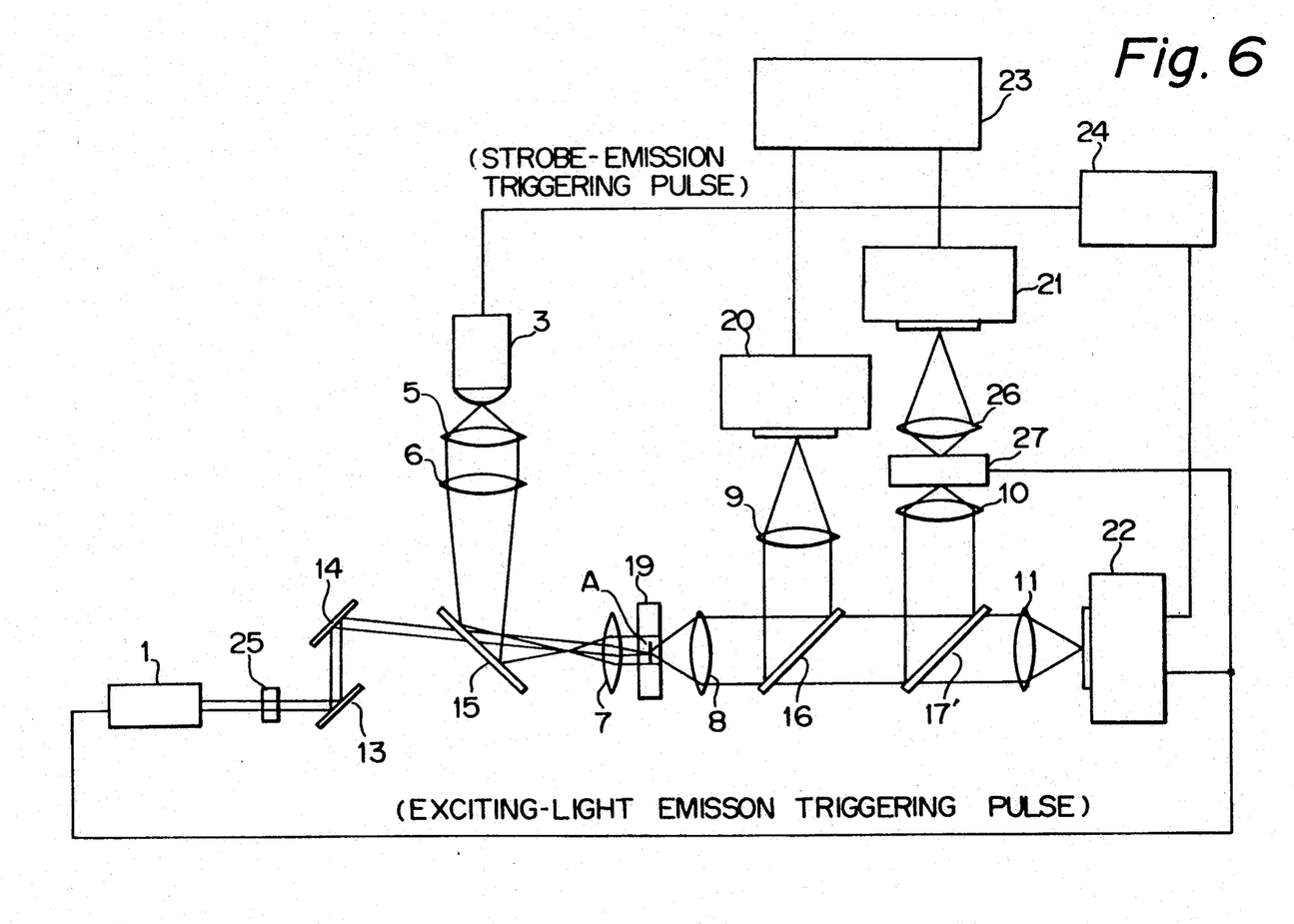
FIG. 6 is a block diagram illustrating the construction of a flow imaging cytometer according to another embodiment of the present invention.

FIG. 6 illustrates another embodiment of the present invention. This embodiment differs from that of FIG. 1 in that the infrared semiconductor laser 2 used as the cell-monitoring light source in FIG. 1 is deleted and the function thereof is performed by the light source for exciting fluorescence.

Since the optical system for white-light photography is completely unchanged and functions in the same manner described earlier, this system need not be described again. Only the monitoring of cells in the flat specimen stream within the flow cell 19 and the operation for exciting fluorescence will be discussed.

Figure 7:
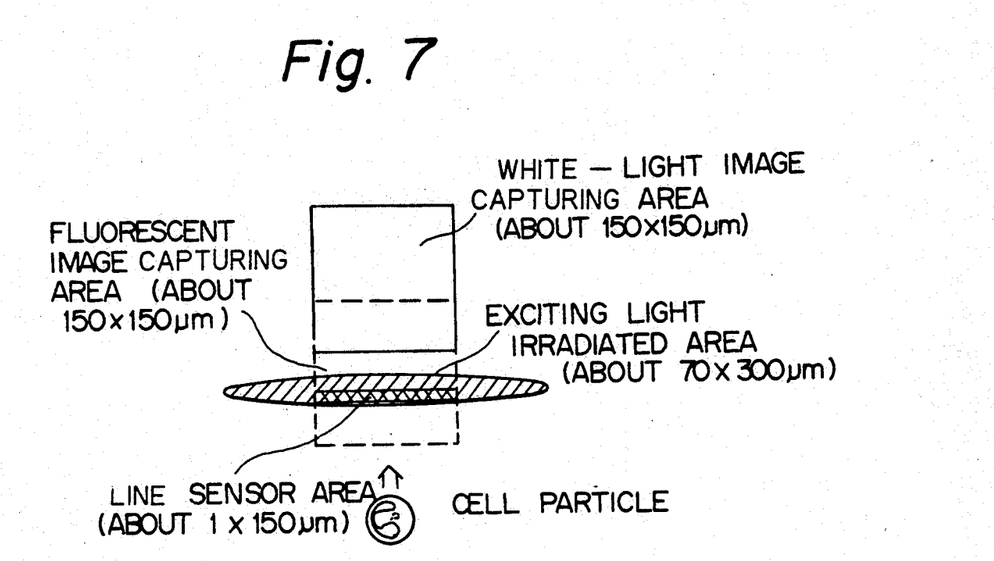
FIG. 7 is a diagram for describing an example of an image capturing area and an irradiation area in a flow cell associated with the cytometer of FIG. 6.
Figure 8:
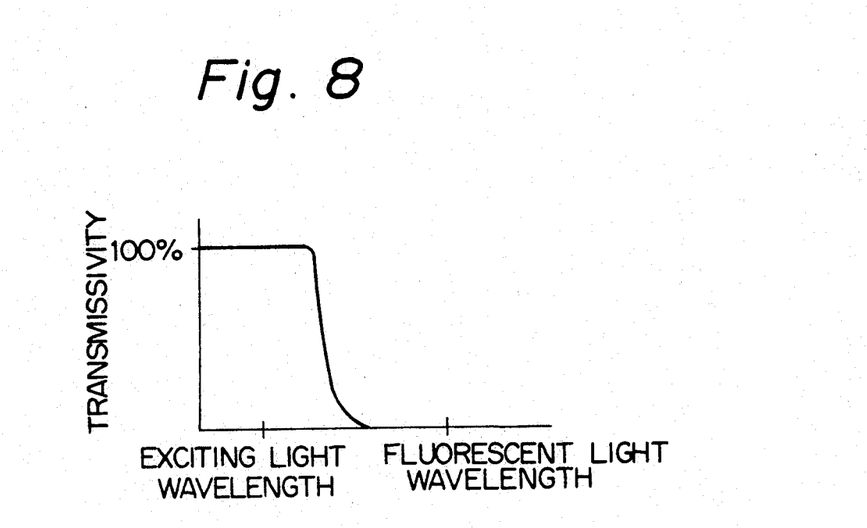
FIG. 8 is a diagram illustrating an example of the characteristic of a dichroic mirror associated with the flow imaging cytometer of FIG. 6.

In this embodiment, the light source 1 for exciting fluorescence emits light continuously, and the light is condensed on the exciting-light irradiated area located on the flat flow A, as shown in FIG. 7. The light source 1 can be made to emit light in two ways. One is for the light source 1 to emit light constantly at a high power, and the other is for the light source 1 to emit a high-power light pulse only when flow-through of a cell is discriminated. The latter method in which the pulsed light emission is used will be described here.

Figure 9:
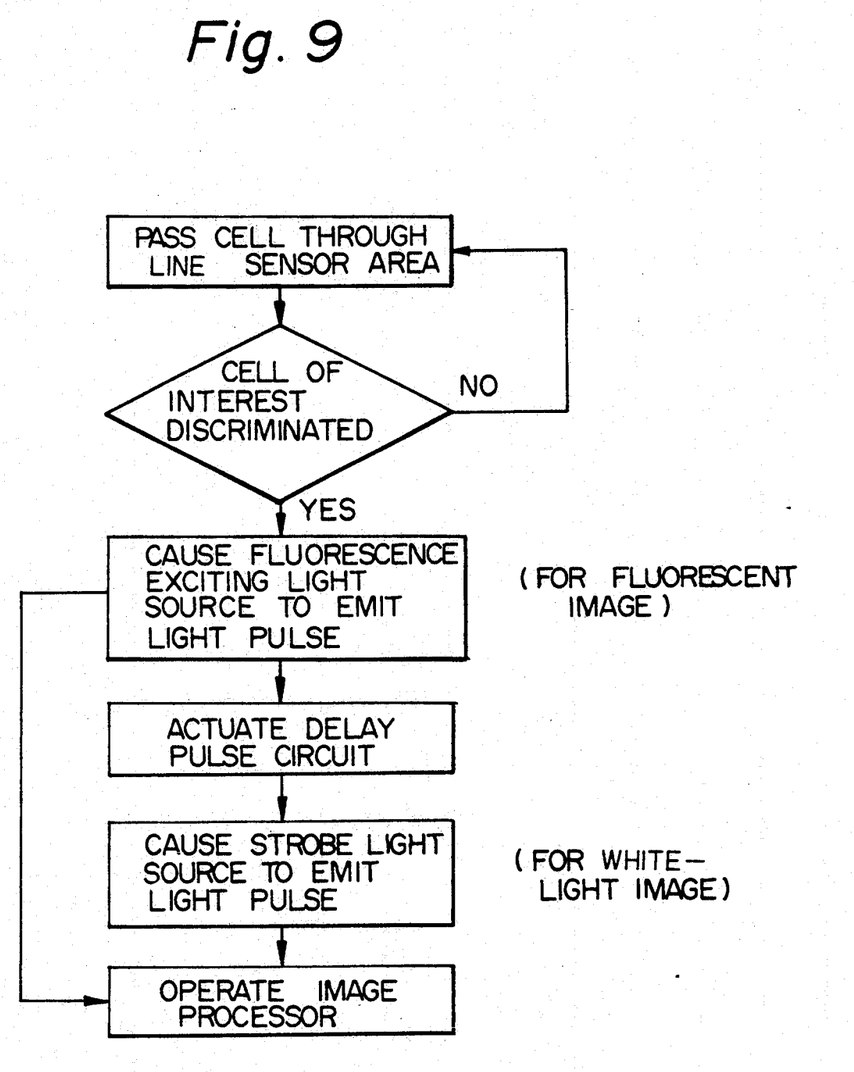
FIG. 9 is a measurement flowchart associated with the flow imaging cytometer of FIG. 6.

As illustrated in FIG. 7, the line sensor area for cell monitoring is disposed at the lower portion of the exciting-light area. When a particle has passed through the line sensor area, it is determined whether the particle is a cell of interest. If a particle is found to be a cell of interest, the light source 1 is caused to emit a high-power light pulse, whereby a fluorescent image of the cell is captured by the video camera 21. This is followed by causing the strobe light source 3 to emit light, whereby a white-light image of the cell is captured by the video camera 20. The flowchart for this photography is illustrated in FIG. 9.

As in the first embodiment, the following values hold:

image capturing area of line sensor: 1 μm × 150 μm
scanning period of line sensor: 33 μsec
flow velocity of sheathed flow: 10 μm/33 μsec
cell size: 15 μm.

If the time from the start of scanning by the line sensor until discrimination of a cell is 100 μsec, then the cell will travel about 30 μm in this period of time. If the area irradiated by the exciting light is set at about 70 × 300 μm, then the first light source 1 is made to emit a high-power light pulse after the cell is detected. The exciting light that has passed through the cell and fluorescent light emitted by the cell passes through the objective lens 8 and half-mirror 16, after which only the fluorescent component is bent at an angle of 90° by the dichroic mirror 17. The fluorescent image is formed on the photoelectric converting surface of the image intensifier 27 by the projecting lens 10. By actuating the image intensifier 27 in synchronization with the exciting-light trigger, the fluorescent image on the photoelectric converting surface is amplified, and the amplified image appears on the output surface of the image intensifier 27. This image is formed on the CCD surface of the video camera 21 by the relay lens 26, whereby a fluorescent image of the cell is obtained.

As in the first embodiment, the light source 3 is made to emit light approximately 500 μsec after discrimination of cell flow-through, whereby a white-light image is obtained by the video camera 20.

The fluorescent image and the white-light image information are subjected to image processing and analysis by the image analyzer 23.

The present invention has the following advantages:

(1) By irradiating a cell of interest with two types of light, two types of images, namely a white-light image and a fluorescent image, of the same cell can be obtained at the same time.

(2) By constantly irradiating cells which pass through the image capturing area, cells of interest can be photographed selectively.

(3) By positionally offsetting the exciting-light irradiated area and the white-light image capturing area from each other, the influence of the exciting light upon the white-light image capturing area is prevented. As a result, it is unnecessary to insert an exciting light cut filter in the white-light image capturing area.

(4) By monitoring passage of cells, the exciting light can be limited to a specific area and the intensity of irradiation per unit area of the exciting light can be increased.

(5) By separating the exciting-light irradiated area and the white-light image capturing area from each other, any wavelength can be selected as the wavelength of the exciting light.

(6) By using flow imaging cytometry, a large number of cells can be measured in a short period of time. As many apparently widely different embodiments of the present invention can be made without departing from the spirit and scope thereof, it is to be understood that the invention is not limited to the specific embodiments thereof except as defined in the appended claims.

What is claimed is:

1. A flow imaging cytometer comprising a flow cell having a flat flow path for causing a specimen solution containing particle components to be sensed to flow as a flat stream, said particle components being treated with a fluorescent stain;

first and third light sources arranged on a first side of said flow cell for irradiating the specimen solution in said flow cell respectively with fluorescence exciting and white pulsed light;

first and third image capturing means arranged on a second side of said flow cell for capturing fluorescent still pictures and white light still pictures of the particle components in the specimen solution irradiated by said first and third light sources, respectively;

a second light source arranged on the first side of said flow cell for irradiating the specimen solution in said flow cell with light constantly;

second image capturing means arranged on the second side of said of said flow cell for capturing an image of the specimen solution irradiated by said second light source;

processing means for executing prescribed analysis based upon image data from said image capturing means; and control means for detecting the particle components based upon the image data from said second image capturing means, and on the basis of such detection, for actuating said first and third light sources after respective minimum time delays, wherein said first and third image capturing means each has a two-dimensional image capturing area on the flow of the specimen solution, the areas are partly overlapped with each other, said second image capturing means has a linear image capturing area on the flow of the specimen solution, the image capturing area of said second image capturing means is formed so as to cross the flow of the specimen solution within the image capturing areas of said first image capturing means, but not within the image capturing area of said third image capturing means, and said first light source is caused to perform irradiation within the image capturing area of said first image capturing means and outside the image capturing area of said third image capturing means.

2. The flow imaging cytometer according to claim 1, wherein said second light source can be one which emits infrared light.

3. The flow imaging cytometer according to claim 1, wherein electronic shutter means are provided in front of the first imaging capture means and including the further step of passing light at said shutter means during emitting of light by said first light source and shielding light at said shutter means during emitting of light by said third light source.

4. A flow imaging cytometer comprising:
a flow cell formed to include a flat flow path for causing a specimen solution containing particle components to be sensed to flow as a flat stream;

a first light source arranged on a first side of said flow cell for irradiating the specimen solution in said flow cell with light the quantity of which is switched;

first image capturing means arranged on a second side of said flow cell for capturing still pictures of particle components in the specimen solution irradiated with high-luminance pulsed light from said first light source;

second image capturing means arranged on the second side of said flow cell for capturing images of the particle components in the specimen solution irradiated continuously with low-luminance light from said first light source;

a second light source arranged on a first side of said flow cell for irradiating the specimen solution in said flow cell with pulsed light;

third image capturing means arranged on the second side of said flow cell for capturing still pictures of particle components in the specimen solution irradiated with light from said second light source;

processing means for executing prescribed analysis based upon image data from said image capturing means; and control means for detecting the particle components based upon the image data from said second image capturing means, and on the basis of such detection, for switching over the luminance of said first light source and actuating said second light source after respective prescribed time delays, wherein said first image capturing means has a two-dimensional image capturing area on the flow of the specimen solution, said second image capturing means has a linear image capturing area on the flow of the specimen solution, the image capturing area of said second image capturing means is formed so as to cross the flow of the specimen solution within said image capturing areas of said first image capturing means, and said first light source is caused to perform irradiation within the image capturing area of said first image capturing means and outside the image capturing area of said third image capturing means.

5. A flow imaging cytometer comprising:
a flow cell formed to include a flat flow path for causing a specimen solution containing particle components to be sensed to flow as a flat stream, said particle components being treated with a fluorescent stain;

a first light source arranged on a first side of said flow cell for irradiating the specimen solution in said flow cell with fluorescent light the quantity of which is switched;

first image capturing means arranged on a second side of said flow cell for capturing fluorescent still pictures of particle components in the specimen solution irradiated with high-luminance pulsed light from said first slight source;

second image capturing means arranged on the second side of said flow cell for capturing images of the particle components in the specimen solution irradiated continuously with low-luminance light from said first light source;

a second light source arranged on a first side of said flow cell for irradiating the specimen solution in said flow cell with pulsed white light;

third image capturing means arranged on the second side of said flow cell for capturing white light still pictures of particle components in the specimen solution irradiated with light from said second light source;

processing means for executing prescribed analysis based upon image data from said image capturing means; and control means for detecting the particle components based upon the image data from said second image capturing means, and on the basis of such detection, for switching over the luminance of said first light source and actuating said second light source after respective minimum time delays, wherein said first and third image capturing means each has a two-dimensional image capturing area on the flow of the specimen solution, the areas are partly overlapped with each other, said second image capturing means has a linear image capturing area on the flow of the specimen solution, the image capturing area of said second image capturing means is formed so as to cross the flow of the specimen solution within said image capturing areas of said first image capturing means but not within the image capturing areas of said third image capturing means, and said first light source is caused to perform irradiation within the image capturing area of said first image capturing means and outside the image capturing area of said third image capturing means.

6. The flow imaging cytometer according to claim 5, wherein electronic shutter means are provided in front of the first imaging capture means and including the further step of passing light at said shutter means during emitting of light by said first light source and shielding light at said shutter means during emitting of light by said second light source.

* * * * *